U S009880095B2

(12) United States Patent
Davis et al.

(10) Patent No.: US 9,880,095 B2
(45) Date of Patent: Jan. 30, 2018

(54) LASER BASED SYSTEM FOR BITUMEN CONTENT DETERMINATION, E.G., USING DISCRETE WAVELENGTH SPECTROSCOPIC ANALYSIS

(71) Applicant: CiDRA Corporate Services Inc., Wallingford, CT (US)

(72) Inventors: Michael A. Davis, Glastonbury, CT (US); Mark R. Fernald, Enfield, CT (US)

(73) Assignee: CiDRA Corporate Services, Inc., Wallingford, CT (US)

(*) Notice: Subject to any disclaimer, the term of this patent is extended or adjusted under 35 U.S.C. 154(b) by 0 days.

(21) Appl. No.: 14/360,813

(22) PCT Filed: Nov. 29, 2012

(86) PCT No.: PCT/US2012/066996
§ 371 (c)(1),
(2) Date: May 27, 2014

(87) PCT Pub. No.: WO2013/082248
PCT Pub. Date: Jun. 6, 2013

(65) Prior Publication Data
US 2014/0326885 A1    Nov. 6, 2014

Related U.S. Application Data

(60) Provisional application No. 61/564,508, filed on Nov. 29, 2011.

(51) Int. Cl.
*G01N 21/3563*    (2014.01)
*G01N 33/24*    (2006.01)
(Continued)

(52) U.S. Cl.
CPC ........ *G01N 21/3563* (2013.01); *G01N 33/24* (2013.01); *G01N 33/241* (2013.01);
(Continued)

(58) Field of Classification Search
CPC .................. G01N 21/3563; G01N 21/359
See application file for complete search history.

(56) References Cited

U.S. PATENT DOCUMENTS 4,337,396 A * 6/1982 Lauer ................. G01N 21/3563
250/255
4,433,239 A * 2/1984 Thompson ............... G01V 8/02
250/255

(Continued)

*Primary Examiner* — Christine Sung
(74) *Attorney, Agent, or Firm* — Ware, Fressola, Maguire & Barber LLP

(57) ABSTRACT

The present invention provides a technique that uses discrete wavelengths of illumination of an ore sample, and through the use of optical filters and laser illumination the signal-to-noise ratio of the measurement can be greatly improved, and may take the form of apparatus featuring a signal processor configured to: receive signaling containing information about a spectral reflectance caused by discrete wavelengths illuminating an ore sample; and determine information about a bitumen content of the ore sample based at least partly on the signaling. The signal processor may provide corresponding signaling containing information about the bitumen content of the ore sample, including for further processing, printing or displaying.

24 Claims, 2 Drawing Sheets

(51) Int. Cl.
*G01N 21/39* (2006.01)
*G01N 21/84* (2006.01)

(52) U.S. Cl.
CPC ............ *G01N 21/39* (2013.01); *G01N 21/84* (2013.01); *G01N 2201/0691* (2013.01); *G01N 2201/0697* (2013.01); *G01N 2201/12* (2013.01)

(56) References Cited

U.S. PATENT DOCUMENTS

| | | | |
|---|---|---|---|
| 5,742,064 A | 4/1998 | Infante | |
| 5,892,586 A | 4/1999 | Thony et al. | |
| 5,984,998 A | 11/1999 | Ottesen et al. | |
| 6,768,115 B2* | 7/2004 | Mikula | G01N 21/3563 250/339.11 |
| 2003/0205507 A1* | 11/2003 | Mikula | C10G 1/047 208/391 |
| 2004/0084623 A1 | 5/2004 | Long et al. | |
| 2008/0315102 A1* | 12/2008 | Weidmann | G01J 3/02 250/339.01 |
| 2009/0122819 A1 | 5/2009 | Dantuas et al. | |
| 2012/0062895 A1 | 3/2012 | Rao | |
| 2014/0347472 A1* | 11/2014 | Davis | G01N 21/3563 348/135 |

* cited by examiner

Apparatus 10

Signal processor 12 configured to:

receive signaling containing information about a spectral reflectance caused by discrete wavelengths illuminating an ore sample;

determine information about a bitumen content of the ore sample based at least partly on the signaling; and/or provide corresponding signaling containing information about the bitumen content of the ore sample, including for further processing, printing or displaying Other circuits or components 14 to implement the functionality of the signal processor 12, including memory modules, input/output modules, busing architecture and other signal processing circuits, wiring or components

Figure 1

LASER BASED SYSTEM FOR BITUMEN CONTENT DETERMINATION, E.G., USING DISCRETE WAVELENGTH SPECTROSCOPIC ANALYSIS

CROSS-REFERENCE TO RELATED APPLICATIONS

This application corresponds to international patent application Ser. No. PCT/US2012/066996, filed 29 Nov. 2012, which claims benefit to provisional patent application Ser. No. 61/564,508 (CCS-0076), filed 29 Nov. 2011, which is incorporated by reference in their entirety.

BACKGROUND OF THE INVENTION

1. Field of Invention

The present invention relates to techniques for analyzing an ore sample; and more particularly relates to techniques for analyzing an ore sample to determine information about a bitumen content of the ore sample, e.g., including using a laser based system and spectroscopic analysis for use in a bitumen recovery process related to mined oil sands.

2. Description of Related Art

It has been previously disclosed that the bitumen content in a portion of raw ore can be determined through spectral analysis, consistent with that set forth in PCT patent application no. PCT/US12/45942, filed 9 Jul. 2012, which is hereby incorporated by reference in its entirety. The techniques previously disclosed center on the analysis of the reflected optical signals when the ore has been illuminated by a broadband illumination source. The illumination source can be either natural occurring sunlight or artificial light. The most common algorithms that are used in analysis of the ore spectra look at some of the known bitumen absorption bands to determine the amount of absorption that has occurred. Typically, this analysis also uses other absorption bands of materials that are outside of the bitumen bands to be able to reference for the overall levels of light present. Other bands that are used are usually associated with the water or clays that are present in the ore and permit a more accurate determination of the bitumen levels. The real world use of this technique often results in difficult measurements that can vary in accuracy as the overall light levels change. The signal-to-noise ratio of the signals seen by the detector can be very low requiring artificial illumination spread over a large spectral region.

SUMMARY OF THE INVENTION

The present invention provides a spectroscopic analysis technique that uses discrete wavelengths of illumination of an ore sample, and through the use of optical filters and laser illumination the signal-to-noise ratio of the measurement can be greatly improved.

According to some embodiments, the present invention may take the form of apparatus featuring a signal processor configured to:
   receive signaling containing information about a spectral reflectance caused by discrete wavelengths illuminating an ore sample; and
   determine information about a bitumen content of the ore sample based at least partly on the signaling.
The present invention may include one or more of the following features:

The signal processor may be configured to determine the information about the bitumen content of the ore sample based at least partly on spectroscopic analysis or processing of the signaling.

The signal processor may be configured to provide corresponding signaling containing information about the bitumen content of the ore sample, including for further processing, printing or displaying.

The signal processor may be configured to determine information about the bitumen content of the ore sample based at least partly on dips in the spectral reflectance in the discrete wavelengths illuminating the ore sample.

The discrete wavelengths may be provided by two lasers, including where each is configured to focus a respective discrete wavelength to illuminate the ore sample. The apparatus may include the two lasers, according to some embodiments of the present invention.

The discrete wavelengths may include at least one wavelength in a 1750 nanometer (nm) region or a 2330 nm region, which both correspond to absorption bands of bitumen.

The signal processor may be configured to implement a 2-band analysis algorithm, including comparing a bitumen reflectance band to an adjacent absorption band for naturally occurring clays in the ore sample.

The bitumen reflectance band may be about 2330 nm and the adjacent absorption band may be about 2220 nm.

The spectral reflectance may be filtered so as to filter out unwanted light. For example, the apparatus may include narrow band optical filters that are centered to discrete laser wavelengths and used to filter out the unwanted light, according to some embodiments of the present invention.

The signal processor may be configured to use directly the signaling detected to calculate or determine the bitumen content of the ore sample.

The lasers may be paired with matching optical filters to achieve an improved signal-to-noise. The apparatus may include the matching optical filters, according to some embodiments of the present invention.

The apparatus may include a tunable laser configured to provide the discrete wavelengths illuminating the ore sample. The apparatus may also include a tunable filter configured to tunably filter the spectral reflectance.

The signaling may be received from a detector configured to respond to the spectral reflectance and provide the signaling detected. The apparatus may include the detector, according to some embodiments of the present invention.

The signal processor may be configured to receive the signaling from a combination of an optical filter and a detector. For example, the optical filter is configured to respond to the spectral reflectance and provided a filtered spectral reflectance, and the detector is configured to respond to the filtered spectral reflectance and provide the signaling in the form of detected and filtered spectral reflectance signaling. The apparatus may include the combination of the optical filter and detector, according to some embodiments of the present invention.

The apparatus may include at least one laser configured to receive a modulation signal and provide a modulated laser beam in the form of a discrete modulated laser wavelength; and a lock-in amplifier used to extract the modulated laser beam only provided from the at least one laser.

The lasers may be configured to be alternatively pulsed and encoded so as to improve discrimination. For example, the lasers may be configured to receive a frequency modulation signal so as to spread a respective laser spectral width provided from the lasers.

The apparatus may include optics configured to enlarge respective spot diameters of laser beams in order to illuminate a larger ore body than may otherwise be possible without using the optics.

The lasers may be configured to be scanned over an area of interest, so that by scanning laser beams, an increased signal-to-noise ratio of the signaling detected can be maintained and still a large area can be scanned.

According to some embodiments of the present invention, the signal processor may include a combination of at least one processor and at least one memory including computer program code, where the at least one memory and the computer program code are configured, with the at least one processor, to cause the apparatus at least to receive the signaling and determine the information about the bitumen content of the ore sample based at least partly on the signaling received, e.g., including in a bitumen recovery process related to mined oil sands.

According to some embodiments, the present invention may include, or take the form of, a method or process that includes steps for receiving in a signal processor signaling containing information about a spectral reflectance caused by discrete wavelengths illuminating an ore sample; and determining information about a bitumen content of the ore sample based at least partly on the signaling. The method may also includes one or more of the features set forth herein, according to some embodiments of the present invention.

BRIEF DESCRIPTION OF THE DRAWING

The drawing includes FIGS. 1-3, which are not necessarily drawn to scale, as follows:

FIG. 1 is a block diagram of apparatus, according to some embodiments of the present invention.

DETAILED DESCRIPTION OF BEST MODE OF THE INVENTION

FIG. 1: The Basic Apparatus 10

FIG. 1 shows apparatus 10 having a signal processor 12 configured to receive signaling containing information about a spectral reflectance caused by discrete wavelengths illuminating an ore sample; and determine information about a bitumen content of the ore sample based at least partly on the signaling, including for use in a bitumen recovery process related to mined oil sands.

The signal processor 12 may also be configured to provide corresponding signaling containing information about the bitumen content of the ore sample, including for further processing, printing or displaying, as well as for other uses either now known or later developed in the future. The scope of the invention is not intended to be limited to the type or kind of use of the corresponding signaling containing information about the bitumen content of the ore sample.

The apparatus 10 may also include other circuits or components 14 to implement the functionality of the signal processor 12 either now known or later developed in the future, e.g., including memory modules, input/output modules, busing architecture and other signal processing circuits, wiring or components, consistent with that set forth herein.

Figure 2:
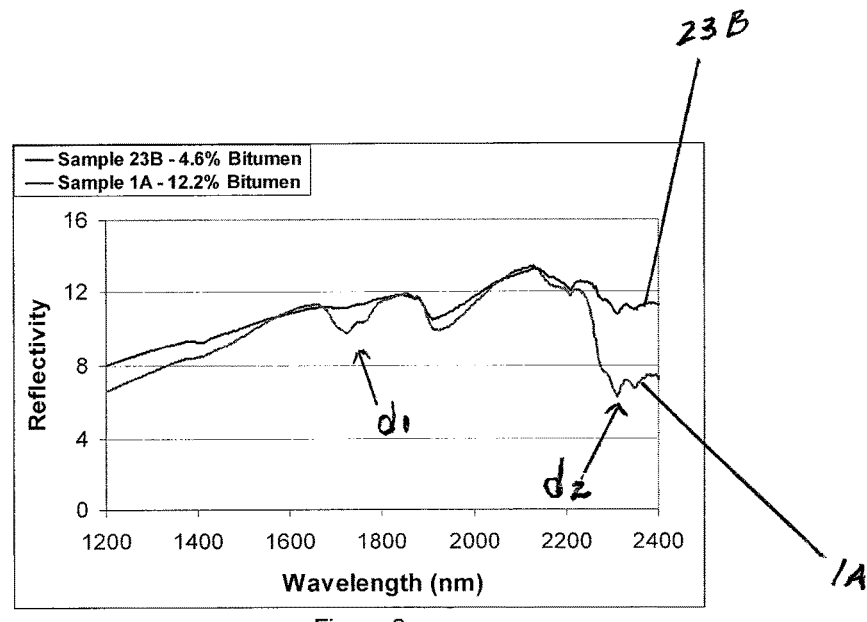
FIG. 2 is a graph of reflectivity versus wavelength (nm) of data points related to two ore samples, including a first sample function (having data points starting at 1200 nm and about 8 reflectivity) with 4.6% bitumen and labeled 23B, and a second sample function (having data points starting at 1200 nm and about 6.5 reflectivity) with 12.2% bitumen and labeled 1A.

FIG. 2: The Graph of Spectral Reflectance

FIG. 2 shows a graph of a spectral reflectance from some bitumen rich ore sample of interest. Bitumen has absorption bands in both a 1750 nm and 2330 nm region as can be seen from dips generally indicated by arrows $d_1$ and $d_2$ in the spectral reflectance in these regions in FIG. 2. In a traditional 2-band analysis algorithm, a 2330 nm bitumen band reflectance may be compared to an adjacent 2220 nm absorption for naturally occurring clays in the ore. The signal processor 12 in FIG. 1 may be configured to implement such a traditional 2-band analysis algorithm without undue experimentation, consistent with that disclosed herein, and as would be appreciated by a person skilled in the art. By way of example, to specifically target these absorption bands, two (2) discrete lasers may be used that have nominal discrete wavelengths of about 2220 nm and 2330 nm respectively, consistent with that shown in FIG. 3 and described below.

Figure 3:
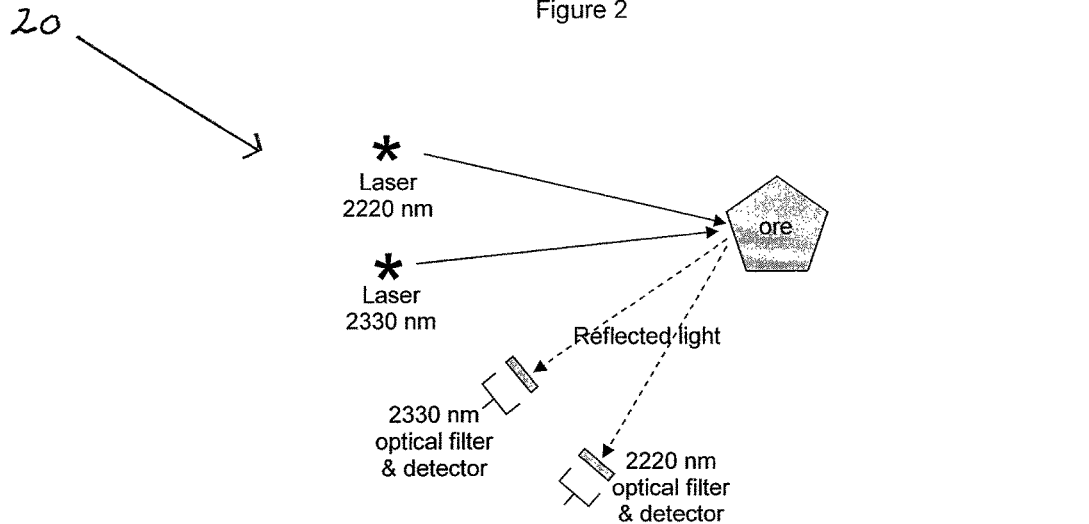
FIG. 3 is a diagram of one system setup having 2220 nm and 2330 nm lasers and 2220 nm and 2330 nm optical filters and detectors, according to some embodiments of the present invention.

FIG. 3: Example of a System Setup

FIG. 3 shows, by way of example, a proposed system setup generally indicated as 20, according to some embodiments of the present invention. As shown, outputs from the two lasers may be focused on the ore sample of interest. In FIG. 3, one laser may take the form of a 2220 nm laser, and the other laser may take the form of a 2330 nm laser. As shown, the laser beams from the two lasers illuminate the ore sample, and are reflected off the ore sample as reflected light. Narrow band optical filters which are centered to respective discrete laser wavelengths can then be used to filter out unwanted light. In FIG. 3, one optical filter and detector combination may include, or take the form of, a 2220 nm optical filter and detector, and the other optical filter and detector combination may take the form of a 2330 nm optical filter and detector. Now the signals detected can be directly used and processed, e.g., by the signal processor 12 in FIG. 1, to calculate or determine the bitumen content of the ore sample of interest. Moreover, an improved signal-to-noise ratio may be achieved through the use of laser light paired with matching optical filters, according to some embodiments of the present invention.

A similar setup system may be implemented in relation to an adsorption band for the 1750 nm region. By way of example, a 1640 nm laser and a 1750 nm laser may be used in combination with a 1640 nm optical filter and detector, and a 1750 nm optical filter and detector.

It is noteworthy that the scope of the invention is not intended to be limited to lasers, optical filters and detectors having these exact or specific optical wavelengths for implementing the aforementioned setup systems related to the 1750 and 2330 adsorption bands. For example, embodiments are envisioned using lasers, optical filters and detectors having slightly higher or lower wavelengths in nm within the spirit of the underlying invention.

By way of example, embodiments are also envisioned in which this same technique can be used with other analysis models, e.g., such as a 5-band model. However, it is also appreciated that this can become impractical when too many bands are used if individual lasers and/or filters are used.

By way of example, an alternative approach may be to use a tunable laser to interrogate the discrete wavelength bands of interest and either a tunable filter or a different discrimination technique, according to some embodiments of the present invention. One such different discrimination technique may utilize, or take the form of, a modulation applied to the laser signal and a lock-in amplifier used to extract only the modulated laser signal being provided from the laser.

By way of example, embodiments are also envisioned in which various other modulation techniques can be used to help increase the signal-to-noise ratio of the detected laser signal as well as other modifications to the laser and detector configuration. For example, according to some embodiments of the present invention, the lasers can be alternatively pulsed and encoded to help improve discrimination, as well as a slight frequency modulation to spread the laser spectral width.

By way of example, since a laser will typically have a small spot size, embodiments are also envisioned in which a larger ore sample or body of interest can be illuminated through the use of optics to enlarge the spot size or diameter, or preferably the laser spot can be scanned over an area of interest on the ore sample or body. By scanning the laser beam, an increased signal-to-noise ratio of the detected signal can be maintained and still a large area can be scanned.

Signal Processor or Signal Processing Module 12

By way of example, and consistent with that described herein, the functionality of the signal processor, device or module 12 may be implemented to receive the signaling, process the signaling therein and/or provide the corresponding signaling, using hardware, software, firmware, or a combination thereof, although the scope of the invention is not intended to be limited to any particular embodiment thereof. In a typical software implementation, the signal processor may include, or take the form of, one or more microprocessor-based architectures having a microprocessor, a random access memory (RAM), a read only memory (ROM), input/output devices and control, data and address busing architecture connecting the same. A person skilled in the art would be able to program such a microprocessor-based implementation to perform the functionality set forth herein, as well as other functionality described herein without undue experimentation. The scope of the invention is not intended to be limited to any particular implementation using technology either now known or later developed in the future. Moreover, the scope of the invention is intended to include a signal processor as either part of the aforementioned apparatus, as a stand alone module, or in the combination with other circuitry for implementing another module.

Techniques for receiving signaling in such a signal processor, device or module 12 are known in the art, and the scope of the invention is not intended to be limited to any particular type or kind thereof either now known or later developed in the future. Based on this understanding, a person skilled in the art would appreciate, understand and be able to implement and/or adapt the signal processor, device or module 12 without undue experimentation so as to receive the signaling containing information about the spectral reflectance caused by discrete wavelengths illuminating the ore sample, consistent with that set forth herein.

Techniques, including techniques based on spectroscopic analysis or signal processing, for determining information based on analyzing or processing signaling received in such a signal processor, device or module 12 are also known in the art, and the scope of the invention is not intended to be limited to any particular type or kind thereof either now known or later developed in the future. Based on this understanding, a person skilled in the art would appreciate, understand and be able to implement and/or adapt the signal processor, device or module 12 without undue experimentation so as to determine information about the bitumen content of the ore sample based at least partly on the signaling received containing information about the spectral reflectance caused by discrete wavelengths illuminating the ore sample, consistent with that set forth herein.

It is also understood that the apparatus 10 may include one or more other modules, components, processing circuits, or circuitry 14 for implementing other functionality associated with the underlying apparatus that does not form part of the underlying invention, and thus is not described in detail herein. By way of example, the one or more other modules, components, processing circuits, or circuitry may include random access memory, read only memory, input/output circuitry and data and address buses for use in relation to implementing the signal processing functionality of the signal processor, or devices or components, etc.

Spectroscopic Analysis or Processing of Signaling

By way of example, and consistent with that which a person skilled in the art would appreciate and understand, spectroscopic analysis or processing is based on spectroscopy, which generally relates to the production and investigation of spectra. Spectroscopy may also be appreciated and understood to be based on the study of the interaction between matter and radiated energy. Historically, spectroscopy originated through the study of visible light dispersed according to its wavelength, e.g., by a prism. Later the concept was expanded greatly to comprise any interaction with radiative energy as a function of its wavelength or frequency. Spectroscopic data is often represented by a spectrum, a plot of the response of interest as a function of wavelength or frequency.

Techniques for spectroscopic analysis or processing of signaling are known in the art, and the scope of the invention is not intended to be limited to any particular type or kind thereof, either now known or later developed in the future, including that disclosed in the aforementioned PCT patent application no. PCT/US12/45942.

Applications

The present invention may also be used in, or form part of, or used in conjunction with, industrial processes like a mineral extraction processing system for extracting minerals from ore either now known or later developed in the future, including any mineral process, such as those related to processing substances or compounds that result from inorganic processes of nature and/or that are mined from the ground, as well as including either other extraction processing systems or other industrial processes, where the sorting, or classification, of product by size is critical to overall industrial process performance.

The Scope of the Invention

While the invention has been described with reference to an exemplary embodiment, it will be understood by those skilled in the art that various changes may be made and equivalents may be substituted for elements thereof without departing from the scope of the invention. In addition, may modifications may be made to adapt a particular situation or material to the teachings of the invention without departing from the essential scope thereof. Therefore, it is intended that the invention not be limited to the particular embodiment(s) disclosed herein as the best mode contemplated for carrying out this invention.

What is claimed is:

1. A laser-based system for bitumen content determination of an ore sample, comprising:
a laser combination having discrete lasers configured to illuminate the ore sample with discrete laser wavelengths of light specifically targeting and corresponding to a reflectance band and an adjacent absorption band of bitumen;
a detector combination having narrow band optical filters and detectors centered at the discrete laser wavelengths of light and configured to
detect spectral reflectances reflected off the ore sample corresponding to the reflectance band and the adjacent absorption band of bitumen, and
provide signaling containing information about the spectral reflectances detected; and
a signal processor configured to
receive the signaling; and
determine corresponding signaling containing information about a bitumen content of the ore sample by comparing the spectral reflectances detected and associated with the reflectance band and the adjacent absorption band using a 2-band spectroscopic analysis of specifically targeted discrete laser wavelengths of light in combination with narrow band filtering of unwanted light, based at least partly on the signaling received.

2. A laser-based system according to claim 1, wherein the signal processor is configured to provide the corresponding signaling containing information about the bitumen content of the ore sample, including for further processing, printing or displaying.

3. A laser-based system according to claim 1, wherein the signal processor is configured to determine information about the bitumen content of the ore sample based at least partly on dips in the spectral reflectance in the discrete laser wavelengths illuminating the ore sample corresponding to the reflectance band.

4. A laser-based system according to claim 1, wherein each discrete laser is configured to focus a respective discrete laser wavelength to illuminate the ore sample.

5. A laser-based system according to claim 1, wherein the laser combination comprises two discrete lasers, and the detector combination comprises two narrow band optical filters and detectors.

6. A laser-based system according to claim 5, wherein the two discrete lasers are paired with matching narrow band optical filters and detectors to achieve an improved signal-to-noise.

7. A laser-based system according to claim 5, wherein the two discrete lasers are configured to be alternatively pulsed and encoded so as to improve discrimination.

8. A laser-based system according to claim 7, wherein the two discrete lasers are configured to receive a frequency modulation signal so as to spread a respective laser spectral width provided from the two discrete lasers.

9. A laser-based system according to claim 5, wherein the two discrete lasers are configured to be scanned over an area of interest, so that by scanning laser beams, an increased signal-to-noise ratio of the signaling detected can be maintained and still a large area can be scanned.

10. A laser-based system according to claim 1, wherein the discrete wavelengths include at least one discrete wavelength in a 1750 nm or 2330 nm region, which corresponds to absorption bands of bitumen.

11. A laser-based system according to claim 1, wherein the signal processor is configured to implement a 2-band analysis algorithm, including comparing a bitumen reflectance band to an adjacent absorption band for naturally occurring clays in the ore sample.

12. A laser-based system according to claim 11, wherein the bitumen reflectance band is about 2330 nm and the adjacent absorption band is about 2220 nm.

13. A laser-based system according to claim 1, wherein the signal processor is configured to use directly the signaling detected to calculate or determine the bitumen content of the ore sample.

14. A laser-based system according to claim 1, wherein the laser combination comprises tunable lasers configured to provide the discrete laser wavelengths illuminating the ore sample.

15. A laser-based system according to claim 1, wherein the detector combination comprises tunable optical filters and detectors configured to tunably filter the spectral reflectances.

16. A laser-based system according to claim 1, wherein
the laser combination is configured to receive a modulation signal and provide a modulated laser beam in the form of a discrete modulated laser wavelength; and
the laser-based system comprises a lock-in amplifier used to extract the modulated laser beam provided from the laser combination.

17. A laser-based system according to claim 1, wherein the laser-based system comprises optics configured to enlarge respective spot diameters of laser beams in order to illuminate a larger ore body.

18. A laser-based system according to claim 1, wherein the signal processor may be configured to determine the information about the bitumen content of the ore sample based at least partly on spectroscopic analysis or processing of the signaling.

19. A laser-based system according to claim 1, wherein the detector combination comprises:
a first detector and filter combination configured to detect a first spectral reflectance caused by a first discrete wavelength provided by a first laser illuminating the ore sample corresponding to the reflectance band of bitumen; and
a second detector and filter combination configured to detect a second spectral reflectance caused by a second discrete wavelength provided by a second respective laser illuminating the ore sample corresponding to the adjacent absorption band of bitumen.

20. A method for determining a bitumen content of an ore sample using a laser-based system, comprising:
illuminating with a laser combination having discrete lasers the ore sample with discrete laser wavelengths of light specifically targeting and corresponding to a reflectance band and an adjacent absorption band of bitumen;
detecting with a detector combination having narrow band optical filters and detectors centered at the discrete laser wavelengths of light spectral reflectances reflected off the ore sample corresponding to the reflectance band and the adjacent absorption band of bitumen;

providing from the detector combination signaling containing information about the spectral reflectances detected; and receiving in a signal processor the signaling; and determining in the signal processor corresponding signaling containing information about a bitumen content of the ore sample by comparing the spectral reflectances associated with the reflectance band and the adjacent absorption band using a 2-band spectroscopic analysis of specifically targeted discrete laser wavelengths of light in combination with narrow band filtering of unwanted light, based at least partly on the signaling received.

21. A method according to claim 20, wherein the method further comprises providing from the signal processor the corresponding signaling containing information about the bitumen content of the ore sample, including for further processing, printing or displaying.

22. A method according to claim 20, wherein the method further comprises determining information about the bitumen content of the ore sample based at least partly on dips in the spectral reflectances in the discrete laser wavelengths illuminating the ore sample.

23. A laser-based system for bitumen content determination of an ore sample comprising:

two discrete lasers configured to illuminate the ore sample with discrete laser wavelengths of light specifically targeting and corresponding to a reflectance band and an adjacent absorption band of bitumen;

two narrow band filters and detectors centered at the disclosed laser wavelengths of light configured to detect spectral reflectances reflected off the ore sample corresponding to the reflectance band and the adjacent absorption band of bitumen, and provide signaling containing information about the spectral reflectances detected; and a signal processor configured to receive the signaling; and determine corresponding signaling containing information about a bitumen content of the ore sample by comparing spectral reflectances associated with the reflectance band and the adjacent absorption band using an n-band spectroscopic analysis of specifically targeted discrete laser wavelengths of light in combination with narrow band filtering of unwanted light, where n is at least 2, based at least partly on the signaling received.

24. A laser-based system according to claim 23, wherein n equals 2 or 5.

* * * * *